United States Patent [19]

Soldner

[11] 4,245,511
[45] Jan. 20, 1981

[54] ULTRASONIC APPLICATOR FOR ULTRASONIC SCANNING OF BODIES AND METHOD OF USING THE SAME

[75] Inventor: Richard E. Soldner, Erlangen, Fed. Rep. of Germany

[73] Assignee: Siemens Aktiengesellschaft, Berlin & Munich, Fed. Rep. of Germany

[21] Appl. No.: 58,870

[22] Filed: Jul. 19, 1979

Related U.S. Application Data

[63] Continuation of Ser. No. 694,835, Jun. 10, 1976, Pat. No. 4,177,679.

[30] Foreign Application Priority Data

Jun. 30, 1975 [DE] Fed. Rep. of Germany ....... 2529155

[51] Int. Cl.³ .............................................. A61B 10/00
[52] U.S. Cl. ....................................... 73/625; 73/633; 128/660
[58] Field of Search .................. 128/660; 73/626, 642, 73/641, 633, 625; 340/103, 105

[56] References Cited

U.S. PATENT DOCUMENTS

| | | | |
|---|---|---|---|
| 3,251,219 | 5/1966 | Hertz | 128/660 X |
| 3,269,173 | 8/1966 | Von Ardenne | 128/660 |
| 3,470,868 | 10/1969 | Krause et al. | 128/660 |
| 3,990,300 | 11/1976 | Kossoff | 128/660 |

FOREIGN PATENT DOCUMENTS

184000 7/1966 U.S.S.R. .................................. 128/660

OTHER PUBLICATIONS

Kossoff et al., "Journal of the Acoustical Society of Amer.", vol. 44, No. 5 (1968), pp. 1310-1318.

*Primary Examiner*—Kyle L. Howell
*Assistant Examiner*—Michael H. Thaler
*Attorney, Agent, or Firm*—Hill, Van Santen, Steadman, Chiara & Simpson

[57] ABSTRACT

An ultrasonic applicator is illustrated for ultrasonic scanning of internal body regions, particularly for obtaining ultrasonic echo sectional views thereof for medical diagnostic purposes, wherein an ultrasonic transducer system directs sequential pulses of ultrasonic energy along successive beam paths converging toward a virtual focal point, and a planar reflector is interposed to reflect the energy pulses and is inclined at an angle deviating from 90° relative to each incident beam path for the purpose of producing an actual convergence of the reflected beam paths externally of the applicator. The depth of the actual convergence point within the body to be scanned may be varied by means of a longitudinally adjustable acoustic window. The actual convergence point may also be shifted by angular adjustment of the reflector. The convergence of the reflected beam energy to a relatively narrow focus at a selectable distance in front of the acoustic window adapts the applicator to sector scanning of a body region accessible only through a relatively narrow acoustic aperture (e.g., between relatively dense bone structures).

1 Claim, 4 Drawing Figures

ULTRASONIC APPLICATOR FOR ULTRASONIC SCANNING OF BODIES AND METHOD OF USING THE SAME

This is a continuation of application Ser. No. 694,835, filed June 10, 1976, now U.S. Pat. No. 4,177,679.

BACKGROUND OF THE INVENTION

The invention concerns an ultrasonic applicator for ultrasonic scanning, particularly for the purpose of obtaining ultrasonic echo sectional views, such applicator having an ultrasonic transmission and receiving system operable to transmit ultrasonic beam energy so as to scan a desired body region at least in one plane, and utilizing a reflector for the purpose of directing the ultrasonic beam energy along the desired paths for effecting such scanning.

An applicator of this type is prior art from U.S. Pat. No. 3,470,868, for example. The prior art applicator involves a cylindrical parabolic reflector and an ultrasonic transmitting/receiving head arranged for rotation about an axis coincident with the focal line of the reflector, the rotary head assembly also being movable in a longitudinal direction along the focal line. Because of the parabolic contour of the reflector successive pulses of ultrasonic energy which have been emitted from the head assembly toward successive points along such contour are reflected by the latter into a body region which is to be examined along successive parallel beam paths. Thus, during rapid rotation of the ultrasonic head assembly about the focal line, the reflected ultrasonic beam energy scans a body area along mutually parallel lines in each revolution of the head assembly. During corresponding linear imaging of the ultrasonic echo signals, each of which is received from a scanning line in the body area, on the viewing screen of an oscilloscope, a sectional view of the body region which is to be investigated is obtained in the scanning plane. Planes which are parallel to such scanning plane may be imaged by means of a corresponding displacement of the rotating ultrasonic transmitting/receiving head assembly in a direction along the focal line of the parabolic reflector. An additional prior art applicator, which, in a corresponding manner, scans the test object in mutually parallel lines, differs from the applicator as specified by U.S. Pat. No. 3,470,868 in that it contains a rotating deflection mirror in the focal line of the parabolic reflector, instead of a rotating ultrasonic transducer assembly, which rotating mirror serves to initially deflect successive pulses of ultrasonic energy arriving from a stationary transducer into successive incident paths impinging on the parabolic reflector.

Particularly in medical ultrasonic diagnosis, there are body areas of interest which are accessible from the body surface only through relatively narrow acoustic apertures, such as the intermediary spaces between the ribs in the case of heart examinations, for example, or, in the case of skull examinations, thin areas of the bone at specific locations on the skull cap, for example a thin bone area above the ear. Ultrasonic scanning processes which operate according to the principle of sector scanning would be advantageous for such applications since, in this case, the required body surface area which is to be contacted by the applicator for the purpose of transmission of the ultrasonic pulses and reception of the echo signals need correspond only approximately to the area required by the ultrasonic transducer head itself.

In order to carry out a sector scanning in the desired manner, scanning procedures would be conceivable wherein the cyclical displacement of the ultrasonic energy over a desired scanning sector is effected electronically by means of a time sequential excitation of a series of ultrasonic generators which are placed in contact with the body, or a single ultrasonic generator might be mechanically guided, for example by hand, over the body for the purpose of cyclical displacement of the ultrasonic beam. Aside from the fact that the direct coupling of a cyclically scanning sound head to a body surface of a patient, for example, is not unproblematical, and, moreover, that the vibration of the ultrasonic generator on the skin surface can bother the patient, the usual disturbances occurring in connection with a direct coupling of a sound head result. Such disturbances include, for example, multiple echos, which occur between strongly reflecting boundary surfaces of the body and the sound head application surface, and which, as superimposed light points in the ultrasonic echo sectional view, make difficult the diagnostic evaluation of the sectional view. In addition, ambiguities can also result due to minor lobes, and there is the disadvantage of dead zones in the coupling area, since the direct coupling of the strong transmission pulse prevents an echo indication from this close range.

An additional disturbing disadvantage results where the intersecting or focal point of the ultrasonic beam paths is external to, or on, the body surface. If the acoustic aperture is located in the interior of the body, such as the space between ribs, for example, which, in certain circumstances, may be located in the body at a depth of up to several centimeters, the potential advantage of sector scanning would be realized only to a very limited extent.

SUMMARY OF THE INVENTION

It is an object of the invention to disclose an application system for the purpose of ultrasonic sector scanning which overcomes the problems and disadvantages set forth in the preceding section.

As specified by the present invention, this object may be realized with an ultrasonic transducer generally of the rotary type initially cited providing that the ultrasonic transmission/receiving system is constructed to direct the ultrasonic energy along successively offset paths which converge toward a first target point common to all of the paths (said first target point or virtual focal point being located outside of the body which is to be scanned), and providing that the ultrasonic transducer system is associated with a planar reflector arranged in the beam paths between the transducer system and said first target point, the reflection surface of said planar reflector being inclined at an angle deviating from 90° as compared with the direction of each incident beam path (which extends toward the first target point), for the purpose of deflecting the ultrasonic beam to a second target point inside the body, (which second target point or actual point of convergence is likewise common to all of the beam paths).

In the ultrasonic applicator as specified by the invention, the reflector, if correspondingly arranged in the beam paths, makes possible a transfer of the point of actual convergence of the ultrasound beams (i.e., of the second target point) to a freely selectable point in the interior of the body, whereby the sector scanning method may also be applied with good success in the case of deeply located acoustical bone-openings. This capacity for random or arbitrary transfer of the intersection point, however, also makes possible the use of a precursory acoustic path, for example a precursory water path, between the ultrasonic transmitting/receiving system and the surface of the body. If this precursory path is acoustically maintained to provide a path length for the ultrasonic energy only slightly longer than the maximum penetration depth of the ultrasound in the body, multiple echos between the sound head and the body tissue are also suppressed to a great extent in a known fashion. In addition, there is also no dead zone, and ambiguities due to minor lobes are reduced to a minimum.

Other objects, features and advantages of the present invention will be apparent from the following detailed description taken in connection with the accompanying sheet of drawing.

DETAILED DESCRIPTION

Figure 1:
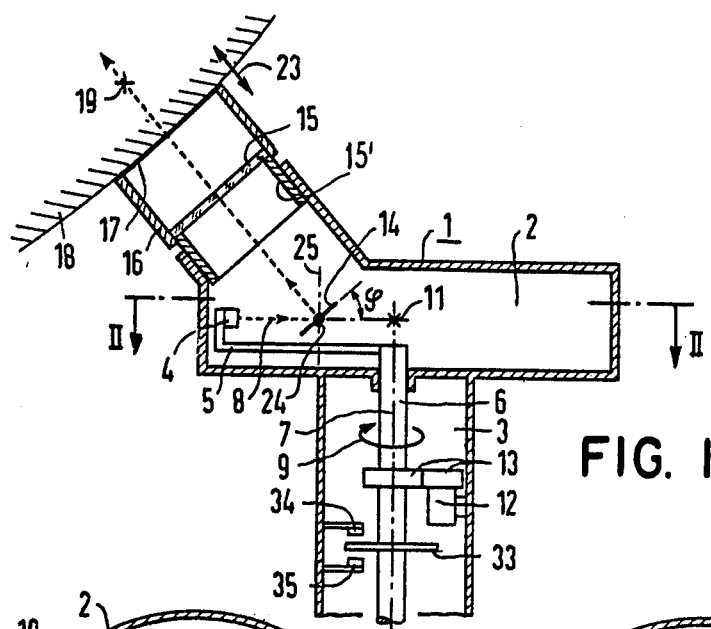
FIG. 1 illustrates an exemplary embodiment of an ultrasonic applicator according to the present invention, in its basic construction, and comprises a diagrammatic partial longitudinal sectional view of the applicator operably coupled to an interior body region for medical diagnostic purposes.
Figure 2:
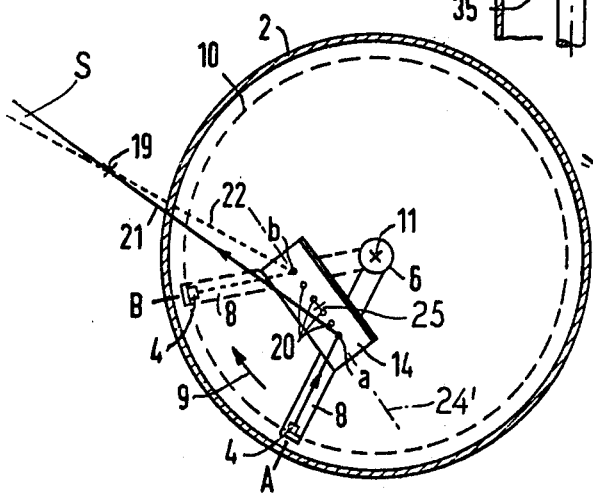
FIG. 2 illustrates a cross section of the ultrasonic applicator of the embodiment according to FIG. 1, taken in the plane indicated by the dot dash lines and in the direction of arrows II—II shown in FIG. 1.

In FIG. 1, the applicator is shown as comprising a housing 1 which is subdivided into compartments 2 and 3 providing respective separate interior spaces. A main part of the compartment 2 is shown in FIG. 2 as having a wall of relatively large diameter circular configuration, by way of example, for accommodating an electromechanical transducer 4. The transducer 4 operates as an ultrasonic transmitter and receiver and is connected with a rotary shaft 6 by means of a support member diagrammatically indicated at 5 in FIG. 1. In the exemplary embodiment, the distance of transducer 4 from the axis of rotation 7 of rotary shaft 6 amounts to a multiple of the rotary shaft diameter. Transducer 4 is oriented to direct an ultrasonic beam 8 radially inwardly, so that the beam 8 follows a path which is essentially perpendicular to the (extended) axis of rotation 7 of rotary shaft 6. During rotation of rotary shaft 6, for example in the direction of arrow 9, the ultrasonic transducer 4 moves in a circular path as indicated by dash line 10 in FIG. 2, about the axis of rotation 7 of rotary shaft 6. Due to this circular motion of the ultrasonic transducer 4 and its radially inwardly directed orientation, the pulses of ultrasonic energy follow successive paths such as those shown for beam 8 in FIGS. 1 and 2, the paths originating at successive points along the circular path 10 while maintaining a radially inward direction toward the axis of rotation 7 of rotary shaft 6. In the particular illustrated embodiment, the beam paths converge toward a target point 11 (virtual focal point) on the axis of rotation 7 of rotary shaft 6 which point 11 is located in the plane of circular path 10 and within the interior of the applicator housing 1. The virtual focal point 11 is shown as being common to all of the beam paths emanating from the transducer 4 and defines a first target point for the ultrasonic beam 8. By way of example, an electric motor 12, in combination with a friction, or a toothed-wheel drive train 13, arranged in compartment 3 of applicator housing 1, may function as the rotary drive for the rotary shaft 6.

In addition, in compartment 2 of applicator housing 1, a planar reflector 14 is arranged in the beam paths between the ultrasonic transducer 4 and the first target point 11 on the axis of rotation 7 of rotary shaft 6, which reflector 14 is inclined at an angle $\phi$, deviating from 90° in relation to the beam 8. The angle $\phi$ is shown in FIG. 1 and is measured in the radial plane containing the beam 8, (such radial plane being normal to the plane of FIG. 2 and containing points A and 11, FIG. 2). Due to its reflection properties, the reflector 14 deflects the ultrasonic beam energy of transducer 4, which has been directed toward target point 11, in the direction of a window 15 of compartment 2 in applicator housing 1, said window 15 being permeable to the ultrasound energy, and being located in offset relation to the shift or sweep plane (defined by circular path 10) of the ultrasonic beam of transducer 4 in the larger diameter part of compartment 2. The acoustic window 15 has a tube 16 movable therewith for adjusting the length of the acoustic path in the compartment 2, said tube being sealed with a membrane 17 which is permeable to the ultrasound energy. In the operating state of the applicator, this membrane 17 functions as a coupling point for the purpose of coupling the applicator to the body surface 18, beneath which, for example, the tissue or organ which is to be scanned is located. The entire compartment 2 of applicator housing 1 including tube 16 is filled with a liquid having good sound-conducting properties; for example, with degassed distilled water. Thus, membrane 17 simultaneously functions as a sealing membrane which prevents leakage of the liquid from the tube 16. Housing 1 of the applicator consists of a material having good sound-absorbing properties, so that ultrasonic waves may issue through the membrane 17 only via window 15.

The mode of operation of the applicator as specified in FIG. 1 is apparent in combination with FIG. 2, as follows:

During rapid rotation, the ultrasonic transducer 4 transmits pulses of ultrasonic energy in the direction of first target point 11. The energy impinging on reflector 14 from the varying directions of the indicent beam paths is then deflected by the latter such that, independently of the respective directions of impingement, the reflected beam paths intersect again at a second intersection point 19 (actual point of convergence) outside of the housing window means 15, 16 and in front of the membrane 17. This second intersection point 19 defines a second common target point for the beam paths and is located in the body tissue which is to be examined. In FIG. 2, the desired deflection action of reflector 14 is indicated on the basis two rotational positions of ultrasonic transducer 4. The first rotational position A defines that position at which ultrasonic transducer 4, rotating in the direction of rotational arrow 9, directs its sound beam 8 precisely onto the reflection surface of reflector 14 (point of impingement a of the sound beam). Rotational position B, with point of impingement b, on the other hand, indicates a position shortly prior to the swinging away of the ultrasonic beam from the reflector. The additional dotted points of impingement 20 on reflector 14 are intermediary reflection points. Each ultrasonic beam deflected from one of these reflection points 20 again follows a reflected beam path which passes through intersection point 19 in the body tissue. Thus, a sector scanning field results, which is bordered on respective sides by reflection beam paths 21 and 22, originating from reflection points a, b. (A scanning sector would be indicated at S for the case where point 19 is located generally at a narrow acoustic aperture in front of the body region to be examined.)

The geometric position of intersection point 19 in the body tissue beneath the skin surface 18 may be readily varied by changing the acoustic path length between transducer 4 and reflector 14, on the one hand, as well as between reflector 14 and separating membrane 17, on the other hand. In the present exemplary embodiment, the acoustic path length between transducer 4 and reflector 14 is advantageously allowed to remain essentially constant, while the membrane tube 16 along with window means 15,15' is arranged such that it can be longitudinally adjusted in the direction toward and away from reflector 14. Through the longitudinal adjustment of tube 16 in the direction of double arrow 23, the depth of intersection point 19 may be readily preselected. Shifting of the sector field S and of the intersection point 19 is additionally possible by changing the angle of inclination $\phi$ of reflector 14 with the use of a rotary knob means 24 (for adjusting the reflector 14 about an axis indicated at 24') or by turning the reflector about an axis 25 which is perpendicular to the incident beam shift or sweep plane in applicator compartment 2. Regarded as a whole, however, the geometric intervals (acoustic path lengths) are always to be correlated with one another such that the precursory water path from transducer 4 via reflector 14 to coupling membrane 17 is, in each case, acoustically somewhat larger than the maximum penetration depth of the ultrasound in the body tissue. In this manner, with a nearly invariable directional characteristic, as well as elimination of any dead space, multiple echos between the transducer and the body tissue are suppressed to a great extent.

In the applicator as specified in FIGS. 1 and 2, the transducer 4 is effective for scanning during traverse of a relatively small arc (i.e., between beam paths 8 incident at a and at b). Therefore, in order to increase the scanning frequency, it is expedient to provide a plurality of ultrasonic transducers, instead of one single rotating transducer 4, for rotational movement by means of rotary shaft 6, the plurality of transducers all being directed toward the common first target point 11 on the axis of rotation 7. These ultrasonic transducers are to be preferably arranged equidistantly with respect to one another on a circle about the rotary shaft, with the axis of rotation as the center.

Figure 3:
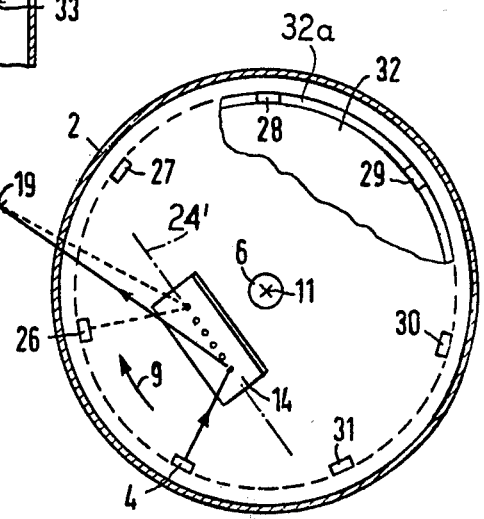
FIGS. 3 and 4 are cross sectional views similar to that of FIG. 2, but showing two modifications of the exemplary embodiment according to FIGS. 1 and 2.

FIG. 3 illustrates an exemplary embodiment of this type, wherein six ultrasonic transducers 26 to 31 are shown along with ultrasonic transducer 4, these transducers being arranged at equal angular intervals on the circumference of a rotary support disk 32 freely rotatable with shaft 6 within compartment 2. The angular intervals are selected such that each time one of the transmitting/receiving transducers (for example, transducer 26 shown in FIG. 3) is just swinging out of the reflection zone of reflector 14, the following transducer (for example, transducer 4 as shown in FIG. 3) is just swinging into the reflection zone of reflector 14. In this manner, an optimum scanning frequency results. For the purpose of correct chronological synchronization of the on- or off-periods for each individual ultrasonic transducer during the swinging into or again out of the reflection zone of reflector 14, respectively, a segmental disk is employed, for example, which is mounted on the rotary shaft 6 and rotates correspondingly with the latter, and which contains segments arranged on its circumference, which segments correspond to the angular arrangement of the individual transducer elements 4, and 26 through 31, on the rotary disk 32, and which segments are permeable, for example, to the light of a light generator (for example, a small incandescent lamp or a light emitting diode). In combination with a light receiver, for example, a photoconductive cell, which is arranged on the opposite side of the segmental disk, a pulse generator results which produces electrical pulses corresponding to the light pulses, and which are synchronized with the arrival of each transducer at points corresponding to A and B in FIG. 2. Each of these electrical pulses can, then, in the same way, function as a switch-on pulse for the ultrasonic transducer assigned to the respective transilluminated part-segment for the purpose of production and reception of ultrasound on the one hand, as well as a switch-off pulse for the previously activated ultrasonic transducer on the other hand. In FIG. 1, the arrangement of a control pulse generator of this type in compartment 3 of the applicator housing is schematically illustrated, the segmental disk being designated by reference numeral 33, the light generator by reference numeral 34, and the light receiver by reference numeral 35.

Figure 4:
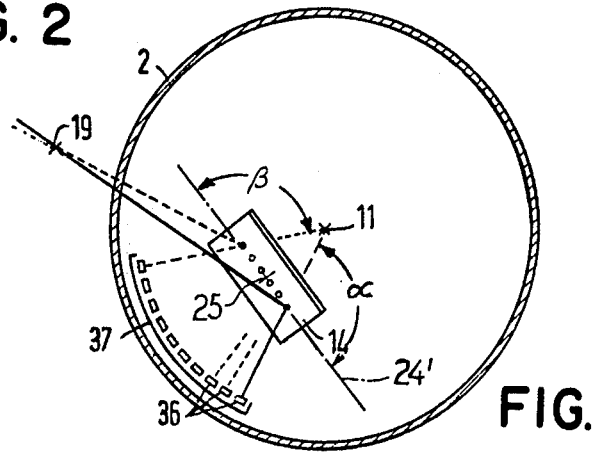

Each of the illustrative embodiments according to FIGS. 1, 2 and 3 comprise applicators with rotating ultrasonic heads. However, the ultrasonic transmission/receiving system may just as well consist of a plurality of indiviual ultrasonic transmitters/receivers, which are stationarily arranged in a circular segmental formation in front of the reflection surface of the reflector, and which, during chronologically successive excitation, focus their respective ultrasonic beams on the center of the circle located behind the reflector. FIG. 4 illustrates an exemplary embodiment of this type, wherein the individual transmitter/receiver elements are designated by reference numeral 36, and a stationary support for the transmitter/receiver elements is designated by reference numeral 37.

While there has been disclosed what are considered to be the preferred embodiments of the invention, many changes and modifications will occur to those skilled in the art based on the teachings of this specification.

SUPPLEMENTARY DISCUSSION CONCERNING THE ILLUSTRATED EMBODIMENTS

In a commercial embodiment of medical diagnostic scanner according to U.S. Pat. No. 3,470,868, each transducer may traverse the parabolic reflector in about seventy milliseconds so that the body-section plane to be examined is scanned by the ultrasonic beam about fifteen times per second. The ultrasound may be emitted in the form of pulses of one microsecond duration with a repetition rate of two thousand per second, for example, so that one hundred and forty pulses are available for each scan. Therefore, the individual image is made up of one hundred and forty parallel lines.

With embodiments such as shown in FIGS. 1–4, operated in an analogous manner, the number of points 20 may similarly be of the order of one hundred, and a corresponding number of transducer elements 36 may be carried by support 37 in FIG. 4. The transducer elements 36 may then be sequentially activated to emit ultrasound pulses so as to accommodate a display rate of about fifteen complete images per second, for example. The number of transducers used according to FIG. 3 may be sufficient to accommodate a similar display rate, and the transducers 4 and 26-31 may be recessed into an upstanding rim structure 32a of disk 32 to accommodate rapid rotation of the transducers without substantial disturbance of the ambient liquid. The mounting of transducer 4 in FIG. 2 may be by means of a similar disk and rim structure, for example.

In each of the embodiments, the reflector 14 may be turned on axis 25 such that a central radial plane (that is the radial plane perpendicular to the plane of FIG. 2 at the radial line bisecting the angle formed by the radial lines from A to 11 and from B to 11) is not at right angles to the axis 24'. In particular, for the case (such as that indicated in FIGS. 2-4) where the distance along the reflected beam path 21 from a to 19 in FIG. 2 is longer than the distance along the reflected beam path 22 from b to 19, the reflector 14 will have been correspondingly turned about axis 25 so that the angle $\alpha$, FIG. 4, is larger than the angle $\beta$ (as measured in the plane of FIG. 4). The smaller cross section part of compartment 2 including window means 15, 16 and 17, may be of circular or other cross section suitable to the desired range of adjustment of the reflected beam paths, and may have its longitudinal central axis extending in a direction intermediate reflected beam paths 21 and 22 and intersecting (when extended) the external target point 19.

Referring to FIG. 2, if the axis 24' of reflector 14 forms equal angles (analogous to angles $\alpha$ and $\beta$ in FIG. 4) relative to the extensions of the outermost beam paths 8 which impinge on the reflector 14, the intersection point 19 will lie on the central radial plane which bisects the sector of incident beam paths. In this case, the center line of the window means 15, 16, 17 may lie in such central radial plane, and FIG. 1 would then represent a longitudinal sectional view taken entirely in a single plane normal to the plane of FIG. 2 and coinciding with the central radial plane which bisects the angle defined by points A, 11, and B in FIG. 2.

The means for accommodating manual adjustment of reflector 14 about axis 24' and/or axis 25 in each of the embodiments is considered adequately indicated by the showing of the axis lines themselves. Such means may, of course, support the reflector 14 from its back side and provide for manual adjustment of the reflector 14 from outside of housing 1 without interference with any rotating parts and without introducing any leakage of the liquid filling compartment 2.

Similarly the means for accommodating manual adjustment of window means 15, 16, 17 is considered to be adequately illustrated in FIG. 1, the sleeve portion 15' of window 15 maintaining a sealing relation during such adjustment. As in the commercial product previously referred to, the membrane 17 may be maintained under tension in the non-loaded condition (i.e. when out of contact with a body surface such as 18). If this is not the case in the commercial product, the water filling must be topped up or replenished. In the present embodiments, a separate filling on tube 16 may be utilized for filling the space between window 15 and membrane 17.

The larger interior space of compartment 2 on the inner side of window 15 may be provided with a suitable pressurized reservoir for accommodating the desired range of longitudinal adjustment of the window means 15, 16, 17.

The maximum body depth from which image-forming echos are received may be about sixteen centimeters, for example, so that the acoustic length of the beam paths within compartment 2 may have a maximum length with window means 15, 16, 17 at a maximum outward limit of adjustment slightly exceeding sixteen centimeters, for example. A sector type display raster may be utilized with sector scanning of a body region such as diagrammatically indicated at S in FIG. 2. Where target point 19 is two centimeters beyond membrane 17, for example, the range of timing adjustment for the echo display may be such as to accommodate display of a scanning sector of any desired radial extent over a range from two to sixteen centimeters in front of membrane 17, for example.

In the illustrated embodiments, the incident beam paths such as indicated at 8 in FIGS. 1 and 2 lie in a common incident beam plane which intersects the reflector 14 at transverse axis 24' thereof. The beam reflecting means such as reflector 14 is of a planar configuration in the direction along transverse axis 24' to provide a narrow focus as indicated at 19 in the plane of the reflected beam paths 21, 22.

It will be apparent that many further modifications and variations may be effected without departing from the scope of the novel concepts of the present invention.

I claim as my invention:

1. An ultrasonic applicator for the ultrasonic scanning of bodies, particularly for the purpose of obtaining ultrasonic-echo-sectional images, comprising an ultrasonic-transmitting/receiving system, whose ultrasonic beam is rotatable in one plane by means of a beam-rotating installation such that successive scanning beam paths have successively different directions as the ultrasonic beam is rotated, and a reflector for causing the ultrasonic beam to be deflected into the body to be examined, wherein the improvement comprises the beam-rotating installation being constructed such that the directions of the successive scanning beam paths are all in alignment with a target point outside the body to be scanned, and the reflector (14) being arranged in the radiation path between the ultrasonic-transmitting/receiving system (4) and the target point (11), said reflector (14) being planar and having a reflection surface inclined at an angle ($\phi$) to the one plane in which the beam (8) is rotated, such angle ($\phi$) deviating from 90° for deflecting the ultrasonic beam to cause the successive scanning beam paths of the deflected beam to converge at an intersection point (19) within the body, the intersection point (19) being common to all the scanning beam paths of the deflected beam, whereby the ultrasonic scan-line-field beyond the common intersection point (19) is the sector-field for the ultrasonic scanning in the body to be examined, and means for predominantly utilizing information from the ultrasonic scan-line-field beyond the common intersection point (19).

* * * * *